(12) United States Patent
Altarac et al.

(10) Patent No.: US 8,048,126 B2
(45) Date of Patent: Nov. 1, 2011

(54) BONE FIXATION ASSEMBLY

(75) Inventors: Moti Altarac, Irvine, CA (US); Lenny Schaust, Delano, MN (US); Philip Mellinger, Ladera Ranch, CA (US)

(73) Assignee: EBI, LLC, Parsippany, NJ (US)

( * ) Notice: Subject to any disclaimer, the term of this patent is extended or adjusted under 35 U.S.C. 154(b) by 0 days.

(21) Appl. No.: 12/606,640

(22) Filed: Oct. 27, 2009

(65) Prior Publication Data

US 2010/0114178 A1     May 6, 2010

Related U.S. Application Data

(63) Continuation of application No. 11/255,138, filed on Oct. 20, 2005, now abandoned.

(51) Int. Cl.
*A61B 17/70*     (2006.01)
(52) U.S. Cl. ...................................................... 606/267
(58) Field of Classification Search .......... 606/267–270, 606/265, 266
See application file for complete search history.

(56) References Cited

U.S. PATENT DOCUMENTS

| | | | |
|---|---|---|---|
| 1,332,626 A * | 3/1920 | Henegar ........................ | 411/539 |
| 5,304,179 A | 4/1994 | Wagner | |
| 5,891,145 A | 4/1999 | Morrison et al. | |
| 6,063,090 A | 5/2000 | Schlapfer | |
| 6,090,111 A | 7/2000 | Nichols | |
| 6,296,642 B1 | 10/2001 | Morrison et al. | |
| 6,485,491 B1 | 11/2002 | Farris et al. | |
| 6,660,004 B2 | 12/2003 | Barker et al. | |
| 6,716,214 B1 | 4/2004 | Jackson | |
| 6,726,689 B2 | 4/2004 | Jackson | |
| 6,835,196 B2 | 12/2004 | Biedermann et al. | |
| 7,686,833 B1 * | 3/2010 | Muhanna et al. ............. | 606/257 |
| 2003/0153911 A1 * | 8/2003 | Shluzas ........................... | 606/61 |
| 2004/0097933 A1 | 5/2004 | Lourdel et al. | |
| 2004/0162560 A1 | 8/2004 | Raynor et al. | |
| 2004/0267264 A1 | 12/2004 | Konieczynski et al. | |
| 2005/0049588 A1 | 3/2005 | Jackson | |
| 2005/0080420 A1 | 4/2005 | Farris et al. | |
| 2005/0177156 A1 * | 8/2005 | Timm et al. .................... | 606/61 |
| 2005/0203516 A1 | 9/2005 | Biedermann et al. | |
| 2006/0129149 A1 | 6/2006 | Iott et al. | |
| 2006/0149240 A1 * | 7/2006 | Jackson ........................... | 606/61 |
| 2006/0235389 A1 * | 10/2006 | Albert et al. ..................... | 606/61 |

OTHER PUBLICATIONS

Office Action (Restriction Requirement) for U.S. Appl. No. 11/255,138, dated Aug. 6, 2008.
Office Action for U.S. Appl. No. 11/255,138, dated Oct. 28, 2008.
Office Action (Final) for U.S. Appl. No. 11/255,138, dated Apr. 28, 2009.
Advisory Action for U.S. Appl. No. 11/255,138, dated Dec. 23, 2009.

* cited by examiner

*Primary Examiner* — Thomas C. Barrett
*Assistant Examiner* — David Bates
(74) *Attorney, Agent, or Firm* — Harness, Dickey

(57) ABSTRACT

A bone fixation assembly and associated method. The bone fixation assembly includes a bone fastener having a head and a bone-engaging portion, a receiver defining an opening along a first axis for receiving the bone fastener at a variable angle, and at least one supporting augment coupled to the bone fastener. The receiver has an inner articulation surface at a lower portion of the opening and matingly articulates with the supporting augment.

22 Claims, 4 Drawing Sheets

BONE FIXATION ASSEMBLY

CROSS-REFERENCE TO RELATED APPLICATIONS

This application is a continuation of U.S. patent application Ser. No. 11/255,138 filed on Oct. 20, 2005. The entire disclosure of the above application is incorporated herein by reference.

INTRODUCTION

Various internal fixation devices are known for correcting and/or stabilizing malformation or other condition of bones, including long bones and the spine. Such fixation devices can include elongated rods affixed with bone screws at desired orientations relative to the bone or spine. Some known bone fixation devices utilize poly-axial or multi-axial screws for adjusting the fixation device at a desired orientation.

Although the existing fixation devices can be satisfactory for their intended purposes, there is still a need for modular bone screw assemblies that can provide variable angle orientation, and which are easy to assemble.

SUMMARY

The present teachings provide a bone fixation assembly. The bone fixation assembly includes a bone fastener having a head and a bone-engaging portion, a receiver defining an opening along a first axis for receiving the bone fastener at a variable angle, and at least one supporting augment coupled to the bone fastener. The receiver has an inner articulation surface at a lower portion of the opening and matingly articulates with the supporting augment.

The present teachings also provide a method for bone fixation. The method includes providing a receiver defining an opening along a first axis for receiving a bone fastener at a variable angle, inserting the head of the bone fastener into the opening, and inserting at least one supporting augment into the opening. The at least one supporting augment is articulable with an inner articulation surface of the receiver. The method further includes coupling the at least one supporting augment to the head of the bone fastener, and varying the angle of the bone fastener relative to the first axis by articulating the at least one supporting augment relative to the articulation surface.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DESCRIPTION OF VARIOUS ASPECTS

The following description is merely exemplary in nature and is in no way intended to limit the invention, its application, or uses.

Figure 1:
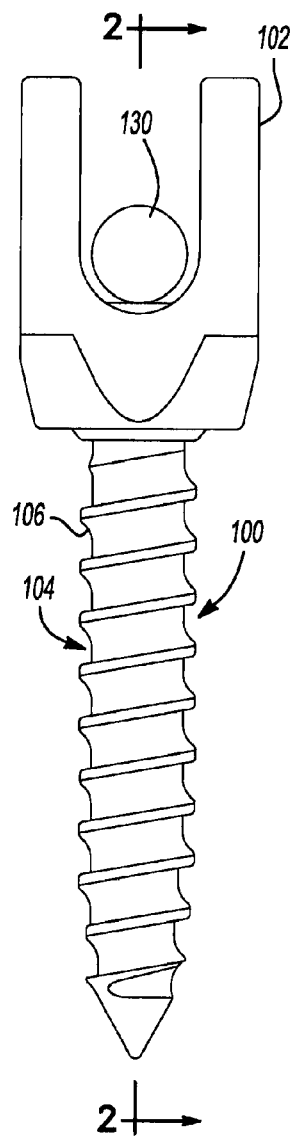
FIG. 1 is a side view of a bone fixation assembly according to the present teachings shown with an elongated fixation member.
Figure 1A:
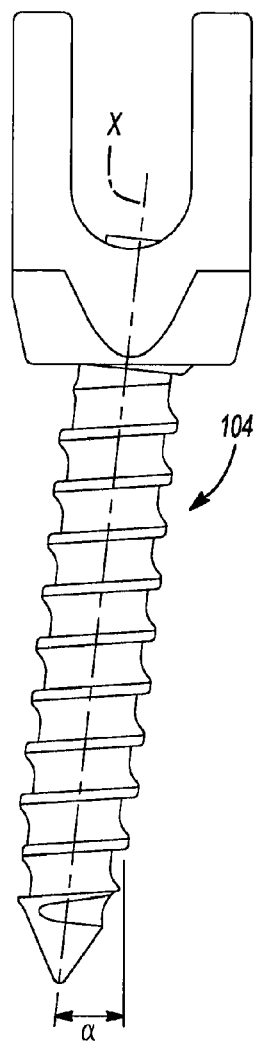
FIG. 1A is a side view of a bone fixation assembly according to the present teachings similar to FIG. 1, illustrating a variable angle orientation.
Figure 2:
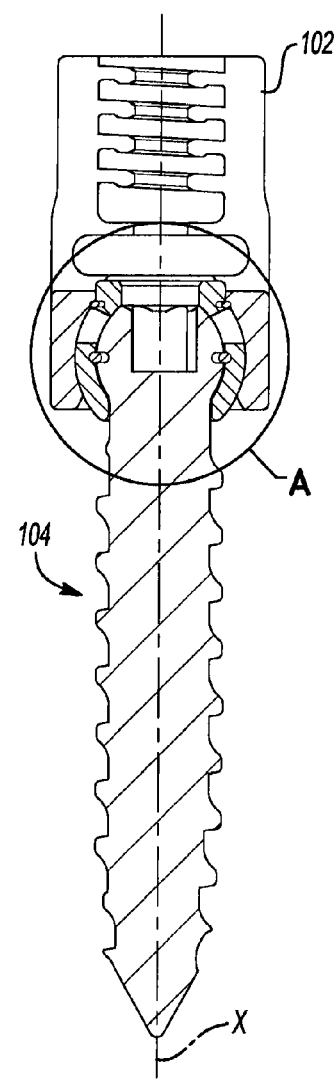
FIG. 2 is a sectional view of the bone fixation assembly of FIG. 1 taken along the axis 2-2 of FIG. 1.
Figure 5:
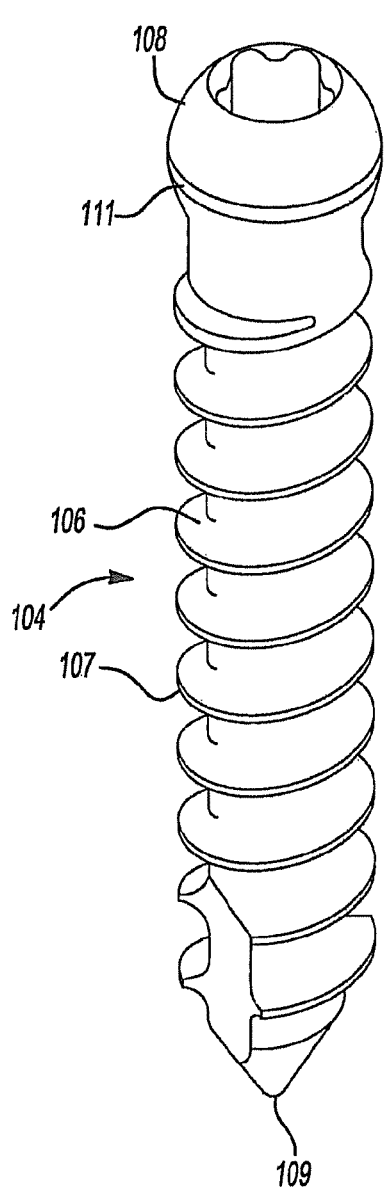
FIG. 5 is an enlarged perspective view of a bone fastener of the bone fixation assembly of FIG. 3.

Referring to FIGS. 1, 1A, and 2, an exemplary variable angle bone fixation assembly 100 is illustrated according to the present teachings. The bone fixation assembly 100 can include a receiver 102 defining an opening 118 along a first axis "X", and a bone fastener 104. The bone fastener 104 can be assembled on the receiver 102 for variable angle angulation relative to the first axis X on an angulation cone of angle α, as illustrated in FIG. 1A. The bone fastener 104 can include a head 108 and a bone-engaging portion 106, which can be shaped as a screw or other anchor, as shown in FIG. 5. The bone-engaging portion 106 can include, for example, a plurality of threads 107 and an anchoring tip 109. The head 108 can include a circumferential exterior groove 111 for engaging a retention member, such as a fastener ring 112, shown in FIG. 9, as discussed below.

Referring to FIGS. 3-10, the receiver 102 can include two substantially parallel arms 126 extending in a direction away from the fastener 104. The arms define a channel 128 along a second axis "Y" generally perpendicular to the first axis X. The channel 128 can be shaped to receive an elongated fixation member 130, such as, for example, a spinal fixation rod or other fixation bar, as shown in FIG. 1. The interior surface of the arms 126 can include a thread pattern or other interlocking form 132, such as a helically-wound interlocking form similar to the one disclosed and described in U.S. Pat. No. 6,726,689, filed Sep. 2, 2002, the disclosure of which is incorporated herein by reference. It will be appreciated that other thread forms can also be used. The interlocking form 132 can mate with a closure member (not shown) having a corresponding interlocking form for securing the fixation member 130 in the receiver 102 such that radial splaying of the arms 126 can be operatively resisted.

Figure 6:
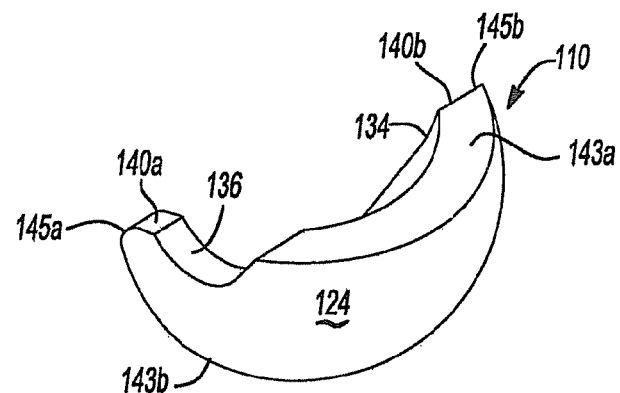
FIG. 6 is an enlarged perspective view of a supporting augment of the bone fixation assembly of FIG. 3.

Referring to FIGS. 3-6, the receiver 102 can include an articulation surface 120 at a lower portion of the opening 118 and adjacent a lower end 122 thereof. The articulation surface 120 can articulate with a corresponding curved exterior surface 124 of one or more discrete supporting augments 110. The conforming articulating surfaces 120, 124 can be portions of generally spherically surfaces or other surfaces that can provide desired variable angle fixation. Each supporting augment 110 can include a curved interior surface 125 which can be shaped to conform to at least a portion of the head 108 of the bone fastener 104. Referring to FIG. 6, in one aspect, each supporting augment 110 can include upper and lower substantially planar surfaces 143a, 143b, first and second oppositely inclined substantially planar end surfaces 140a, 140b, and an upper curved cutout or notch 136 adjacent to first end surface 140a. The upper surface 143a can define a sharp corner 145b with the second end surface 140b, and a blunt or rounded corner 145a with the first end surface 140a.

The supporting augments 110 can be positioned relative to each other such that upon assembly each of the first and second end surfaces 140a, 140b of one supporting augment 110 can mate with the second and first end surfaces 140b, 140a, respectively, of the other supporting augment 110, thereby completing an annular curved surface with a 360-degree circumference. The shape of the supporting augments 110 can be defined for ease of assembly and angulation during assembly. For example, during assembly, the supporting augments 110 can be positioned such that the sharp corner 145b of each supporting augment 110 rides on the notch 136 of the other supporting augment 110, such that the supporting augments 110 overlap partially, and the overall size/volume of the resulting configuration is smaller during assembly than the size of the assembled supporting augments 110.

Figure 3:
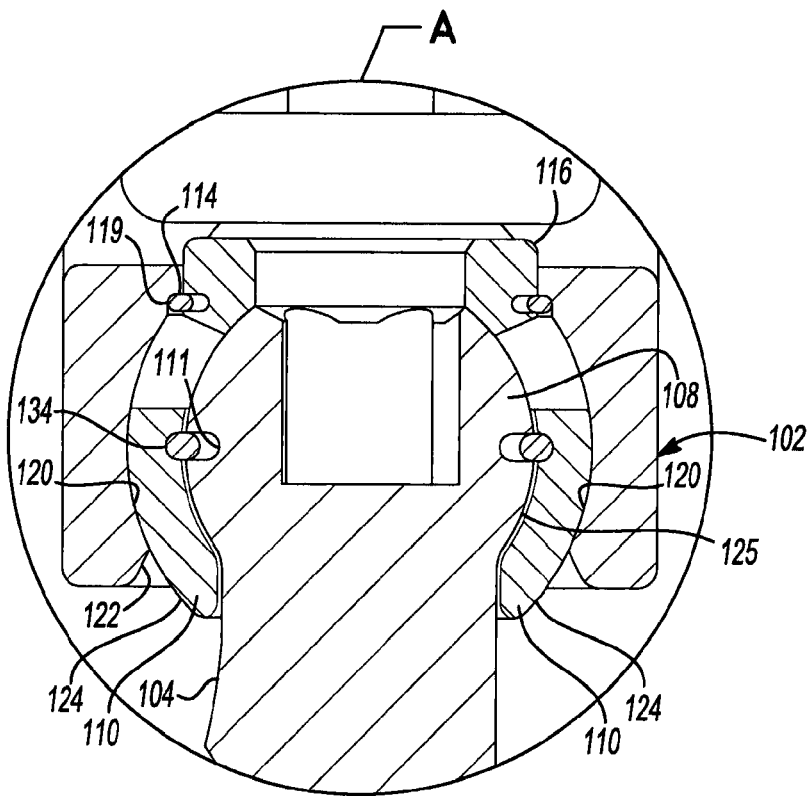
FIG. 3 is an enlarged view of detail A of FIG. 2 shown additionally in exploded view.
Figure 4:
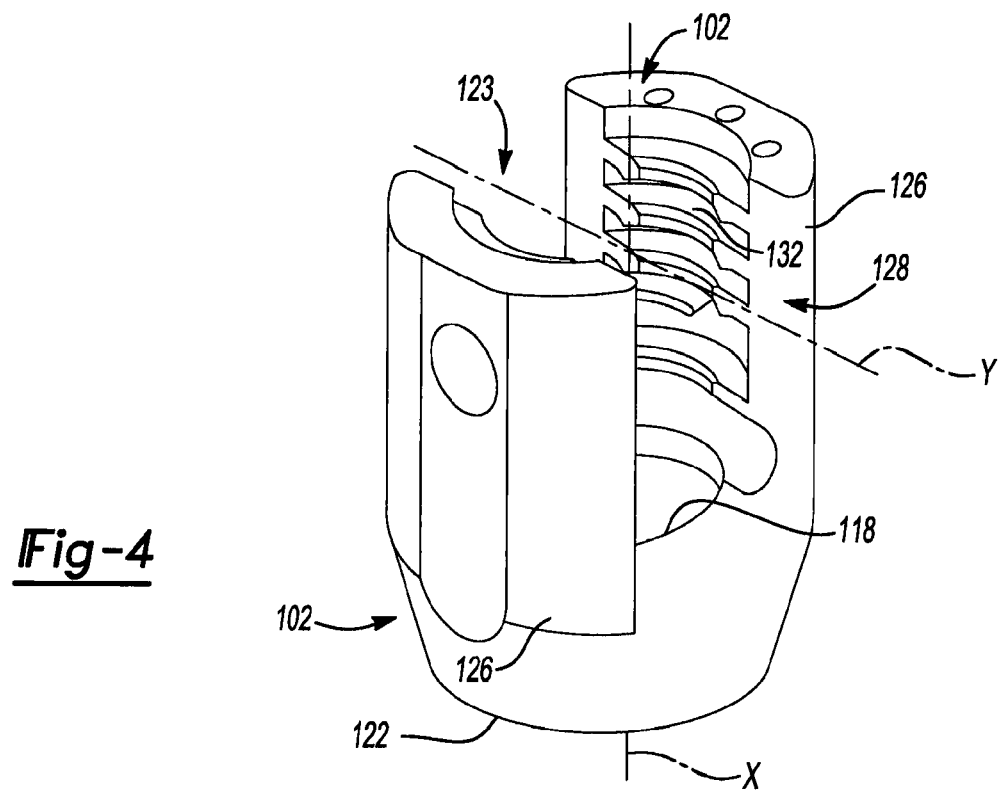
FIG. 4 is an enlarged perspective view of a receiver of the bone fixation assembly of FIG. 3.
Figure 9:
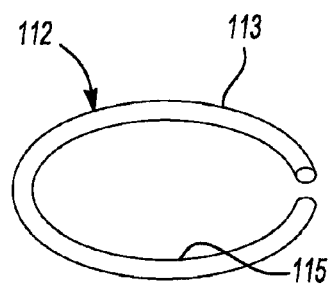
FIG. 9 is an enlarged perspective view of a fastener ring of the bone fixation assembly of FIG. 3.
Figure 10:
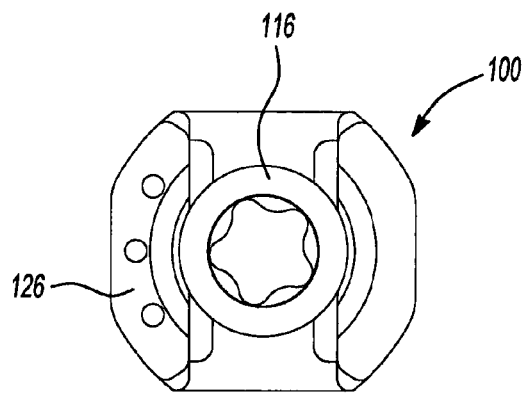
FIG. 10 is an end view of the bone fixation device of FIG. 2.

Referring to FIGS. 3, 6 and 9, each supporting augment 110 can also include a circumferential interior groove 134 shaped for partially receiving the fastener ring 112. The fastener ring 112 can be a substantially flat and compliant split ring with an outer boundary 113 and an inner boundary 115. In assembly, at least a portion of the outer boundary 113 of the fastener ring 112 can be engaged with the interior groove 134 of the supporting augment 110. The inner boundary 115 of the fastener ring 112 can engage the exterior groove 111 of the head 108 of the bone fastener 104.

Figure 7:
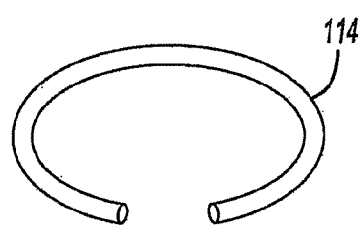
FIG. 7 is an enlarged perspective view of a cap ring of the bone fixation assembly of FIG. 3.
Figure 8:
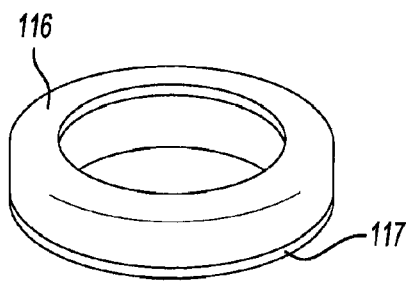
FIG. 8 is an enlarged perspective view of a cap of the bone fixation assembly of FIG. 3.

Referring to FIGS. 3, 7, and 8, the bone fixation assembly 100 can also include a cap 116, which can engage an upper portion of the head 108. The cap 116 can include a circumferential exterior cap groove 117 for engaging a cap ring 114. The cap ring 114 can be a compliant split ring and can be positioned in engagement between the cap groove 117 and an interior groove or slot 119 defined in the receiver 102. Pressing the cap 116 against the head 108 of the bone fastener 104 with the fixation member 130 can prevent angulation of the bone fastener 104 relative to the receiver 102, thereby retaining the fastener 104 in a fixed orientation.

The bone fixation assembly 100 can be assembled during or before the surgical procedure. Generally, the head 108 of the bone fastener 104 can be inserted first into the opening 118. At least one supporting augment 110 can be inserted into the opening 118, and coupled to the head 108 of the bone fastener 104. The angle α of the bone fastener 104 relative to the first axis X can then be varied by articulating the supporting augment 110 relative to the articulation surface 120.

In one exemplary aspect, the fastener ring 112 can be assembled on the exterior groove 111 of the head 108 of the bone fastener 104. The head 108 with the fastener ring 112 thereon can be inserted into the receiver 102 through the lower end 122 of the opening 118, and can be pushed above its final seating position to facilitate assembly, as necessary. The supporting augments 110 can then be inserted from an upper end 123 of the receiver 102 and can be pushed toward the fastener ring 112 while the bone fastener 104 is pulled down, until the supporting augments 110 engage the fastener ring 112 and the bone fastener 104 is seated in engagement with the receiver 102. In this position, the bone fastener 104 can freely angulate relative to axis X, but can not be removed from the receiver 102 either through the lower end 122 or through the upper end 123. For facilitating insertion the supporting augments 110 can be arranged with partial overlapping therebetween, as discussed above. In another aspect, the supporting augments 110 can be inserted into the receiver 102 through the lower end 122 of the opening 118, and manipulated into engagement with the fastener ring 112.

The cap 116 with the cap ring 114 can be inserted from the upper end 123 of the receiver 102 such that the cap ring 114 engages the interior slot 119 of the receiver 102. For a particular application, such as spinal fixation, a rod or other longitudinal fixation member 130 can be positioned along the channel 128 and pressed against the cap 116 with a compression member (not shown). Pressing the cap 116 against the head 108 with the compression member secures the bone fastener 104 in a desired orientation.

It will be appreciated that the modularity and shape of the various parts of the bone fixation assembly 100 can provide a compact (non-bulky) bone fixation device, which can be easily assembled during the surgical procedure, or can also be at least partially pre-assembled. Furthermore, the bone fixation assembly 100 can be easily configured for accommodating various surgical situations at the site of operation as desired by the surgeon.

The fixation assembly can be formed from biocompatible materials, such as, for example, metallic materials.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A bone fixation assembly comprising:
   a bone fastener having a head and a bone-engaging portion;
   a receiver defining an opening along a first axis for receiving the bone fastener at a variable angle, the receiver having an inner articulation surface at a lower portion of the opening; and
   at least two supporting augments coupled to one another and to the bone fastener for movement therewith, the at least two supporting augments being matingly articulable with the articulation surface of the receiver and each including a notch formed in a surface thereof, each notch being open in a direction substantially parallel to the first axis and receiving a portion of the other of the supporting augments to provide an annular curved surface with a three-hundred-and-sixty degree)(360° circumference.

2. The bone fixation assembly of claim 1, wherein the articulation surface is substantially spherical and wherein the supporting augments cooperate to form an outer mating surface that is substantially spherical.

3. The bone fixation assembly of claim 1, wherein a lower end of the opening is configured for receiving the head of the bone fastener therethrough.

4. The bone fixation assembly of claim 3, further comprising a fastener ring, the fastener ring couplable to the head of the bone fastener such that the fastener ring can be inserted assembled to the bone fastener from the lower end of the opening.

5. The bone fixation assembly of claim 4, wherein the fastener ring is supportable on a groove formed in at least one of the supporting augments.

6. The bone fixation assembly of claim 5, wherein the fastener ring is a split ring.

7. The bone fixation assembly of claim 5, wherein at least one of the supporting augments is shaped for allowing variable angulation of the fastener.

8. The bone fixation assembly of claim 7, wherein the supporting augments are further shaped for preventing removal of the fastener when the ring is coupled to the supporting augments and to the head of the fastener.

9. The bone fixation assembly of claim 1, wherein each supporting augment includes a first end having a substantially planar surface.

10. The bone fixation assembly of claim 9, wherein the substantially planar surfaces of the respective supporting augments are oppositely inclined.

11. The bone fixation assembly of claim 9, wherein the substantially planar surfaces provide each supporting augment with an edge that is received within the notch of the other supporting augment once assembled.

12. The bone fixation assembly of claim 1, further comprising a fastener cap for coupling the head of the fastener to an inner surface of the receiver.

13. The bone fixation assembly of claim 11, further comprising a cap ring for coupling the fastener cap and the receiver.

14. The bone fixation assembly of claim 12, wherein the receiver defines a channel extending along a second axis generally perpendicular to the first axis.

15. The bone fixation assembly of claim 13, wherein the channel is shaped for receiving a fixation rod above the fastener cap.

16. The bone fixation assembly of claim 14, wherein the cap ring is a split ring.

17. The bone fixation assembly of claim 1, wherein the at least two supporting augments include a first supporting augment and a second supporting augment.

18. The bone fixation assembly of claim 17, wherein the first supporting augment is matingly attached to the second supporting augment about an axis of the bone fastener.

19. The bone fixation assembly of claim 17, wherein the first supporting augment cooperates with the second supporting augment to surround an outer perimeter of the bone fastener.

20. A bone fixation assembly comprising:
a bone fastener having a head and a bone-engaging portion;
a receiver defining an opening along a first axis for receiving the bone fastener at a variable angle, the receiver having an inner articulation surface at a lower portion of the opening; and
first and second supporting augments coupled to one another and to the bone fastener for movement therewith, the first and second supporting augments being matingly articulable with the articulation surface of the receiver and each including a notch receiving a portion of the other supporting augment in a direction substantially parallel to the first axis during assembly of the first and second augments to the receiver.

21. The bone fixation assembly of claim 20, wherein the first and second supporting augments are at least partially overlapping.

22. The bone fixation assembly of claim 20, wherein the first supporting augment and the second supporting augment cooperate to provide an annular curved surface with a three-hundred-and-sixty degree)(360°) circumference.

* * * * *

UNITED STATES PATENT AND TRADEMARK OFFICE
CERTIFICATE OF CORRECTION

| | | |
|---|---|---|
| PATENT NO. | : 8,048,126 B2 | |
| APPLICATION NO. | : 12/606640 | |
| DATED | : November 1, 2011 | |
| INVENTOR(S) | : Moti Altarac, Lenny Schaust and Philip Mellinger | |

It is certified that error appears in the above-identified patent and that said Letters Patent is hereby corrected as shown below:

Col. 5, Line 16, Claim 13 - "claim 11" should be --claim 12--

Col. 5, Line 19, Claim 14 - "claim 12" should be --claim 13--

Col. 5, Line 22, Claim 15 - "claim 13" should be --claim 14--

Col. 5, Line 25, Claim 16 - "claim 14" should be --claim 13--

Signed and Sealed this

Seventh Day of February, 2012

David J. Kappos
*Director of the United States Patent and Trademark Office*